United States Patent [19]

Hydes et al.

[11] 4,148,870

[45] Apr. 10, 1979

[54] OSMIUM COMPOUNDS

[75] Inventors: Paul C. Hydes; Michael J. Cleare, both of London, England

[73] Assignee: Johnson, Matthey & Co., Limited, London, England

[21] Appl. No.: 905,791

[22] Filed: May 15, 1978

Related U.S. Application Data

[62] Division of Ser. No. 702,132, Jul. 2, 1976, Pat. No. 4,100,158.

[30] Foreign Application Priority Data

Jul. 9, 1975 [GB] United Kingdom ............... 28877/75

[51] Int. Cl.$^2$ .......................... G01N 1/00; G01N 1/28; G01N 1/30
[52] U.S. Cl. ............................................ 424/3; 424/75
[58] Field of Search ....................................... 424/3, 75

[56] References Cited

PUBLICATIONS

Hanker, 33rd Annual Meeting Electron Microscopy Soc. of Amer., Proceedings, vol. 33, Aug. 11, 1975, pp. 456, 457.
Elleder, Chem. Abs., vol. 74, 1971, Ab. No. 50441t.
Hanker, Chem. Abs., vol. 86, 1977, Ab. No. 13469k.
Elvidge, Chem. Abs. vol. 44, 1950 pp. 4007–4008.
Criegee, Chem. Abs. vol. 48, 1954, p. 1239.
Ray, Chem. Abs. vol. 67, 1967, Ab. No. 26263 w.
Chem. Abs., Subject Index, vol. 67, p. 2488s (1967).
D'yachenko, Chem. Abs. vol. 81, 1974, Ab. No. 130291d.

*Primary Examiner*—Anna P. Fagelson
*Attorney, Agent, or Firm*—Cushman, Darby & Cushman

[57] ABSTRACT

This specification describes a complex of osmium tetroxide and a compound having a heterocyclic ring containing one or two tertiary nitrogen atoms. The compound may be an aromatic tertiary amine and the tertiary nitrogen atom may be the sole heterocyclic atom in the heterocyclic ring. The complexes described are suitable for fixing and staining cells and may be used in the preparation of biological specimens for examination by electron microscopy.

3 Claims, No Drawings

OSMIUM COMPOUNDS

This is a division of application Ser. No. 702,132 filed July 2, 1976, now U.S. Pat. No. 4,100,158.

This invention relates to osmium tetroxide complexes, and in particular to complexes suitable for fixing and staining cells, particularly in the preparation of biological specimens for examination by electron microscopy.

The technique of electron microscopy has, in recent years, enabled startling advances in the field of biological research to be made. The principal advantage of the electron microscope is that it can be used to examine objects up to at least a thousand times smaller than a light microscope can resolve, but a disadvantage is that, unlike the light microscope, the electron microscope cannot examine living cells. Biological specimens therefore have to be prepared prior to examination.

One way of preparing specimens is the "histological" method, the aim of which is to preserve the specimen faithfully and exactly as it was in life and to render clearly visible all the inter-relationships between tissues, cells, organelles and macro-molecules. This is achieved by adding to the living cells a substance which will kill the tissues and, at the same time, preserve all the fine structure and prevent any post-mortem reactions or attack by micro-organisms from taking place. This process is known as "fixation". However, the penetrating power of an electron beam is not sufficiently great to traverse a section of the thickness of even a single cell, and so cells must be sliced into sections of 500 Å thick or even thinner.

Having regard to the above constraints, the stages in electron histology are basically as follows:

(i) Fixation: killing the specimen with preservation of the fine structure;

(ii) Block staining: causing certain components of the structure to attract heavy metal ions and thus to scatter electrons differentially in order to render the structure visible in the electron microscope. (Stages (i) and (ii) may be combined);

(iii) and (iv) Dehydration and Infiltration: removing water and replacing it with a fluid which can be hardened by, for example, polymerisation into a solid which is sufficiently elastic to be sliced evenly into sections of thickness 500Å or less;

(v) Polymerisation;

(vi) Sectioning;

(vii) Mounting sections on copper support grids; and (viii) Section staining; increasing the existing differential electron scattering power of the specimen constituents by renoting with solutions of heavy metals.

The primary purpose of the fixative—that is, the substance used to "fix" the specimen—is to solidify the protein sol which flows in the network of phospholipoprotein membranes forming the cell framework. It should also render insoluble all the other chemical constituents of the cell, such as nucleic acids, nucleoproteins, carbohydrates and lipids. The fixative should also provide electron contrast, thus making it possible to combine stages (i) and (ii) in the above-mentioned scheme.

However, it is impossible in practice to satisfy all these conditions with one fixative, but the substance that has hitherto been used most, and which has come closest to satisfying all these conditions, is osmium tetroxide. This substance stabilizes protein sols by chemical combination and formation of cross-linkages and preserves, almost perfectly, coll fine structure. It preserves lipids, phospholipoproteins and nucleoproteins but is a poor preservative for carbohydrates and nucleic acids. Above all, it is an excellent producer of electron contrast. This last property is due to the fact that, since osmium tetroxide fixes by chemical combination rather than precipitation, osmium metal remains in the fixed cell, attached firmly to the structure it stabilizes, thus—due to its extremely high density—delineating the structure almost perfectly in an electron beam. Furthermore, osmium tetroxide does not harden and embrittle fixed tissue, neither does it shrink or swell the fixed tissue.

In practice, specimens are usually subjected to a two-stage fixing procedure, the first stage of which is designed to overcome the few disadvantages possessed by osmium tetroxide. For example, apart from the already-mentioned poor performance in preserving carbohydrates and nucleic acids, osmium tetroxide penetrates tissues only very slowly. The first stage of the two-stage process often consists of an aldehyde fixation, frequently using glutaraldehyde, and the second stage consists of the osmium tetroxide fixation.

The remainder of the stages in the electron histological method of specimen preparation need only be mentioned in passing, because they have no direct relevance to the present invention.

The fluid for the infiltration stage is selected according to the required properties of the resin in which the specimen is ultimately to be embedded. A common type of resin in use today is a thermosetting synthetic epoxy resin, for example "Araldito" (Registered Trade Mark), often with a plasticiser such as dibutyl phthalate added to make the cured resin more suitable for sectioning.

The mounted sections are optionally stained to increase further the differential electron scattering power initially induced by osmium tetroxide. The section is reacted with a solution of a heavy metal salt, for example alkaline lead citrate. Lead is especially useful for staining glycogen, which is unstained by osmium tetroxide. Other stains which may be used for specific purposes are, for example, aqueous or alcoholic uranyl acetate, aqueous or alcoholic phosphotungstic acid and aqueous potassium permanganate.

It is an object of the present invention to provide a more convenient source of osmium for fixing and/or staining cells. Osmium tetroxide is very volatile and the vapour thereof is extremely toxic and, consequently, considerable care must be exercised in its storage, handling and use. It should always be used, for example, in an efficient fume cupboard, with the front pulled down as far as possible, and handled only with rubber gloves. Furthermore, it is usually supplied in sealed vials and, once the vial is opened, it is the general practice to discard what is not immediately required rather than store it for future use.

It is known that one convenient source of osmium tetroxide is the 2:1 addition compound formed from osmium tetroxide and hexamethylene-tetramine, having the molecular formula $C_6H_{12}N_4.2OsO_4$. This compound is a stable crystalline solid, melting at 180°–185° C. and is non-explosive under the influence of heat. One great advantage of this compound is that, in the dry, solid state, the vapour pressure of the osmium tetroxide is extremely low. It may therefore be handled freely on the open laboratory bench and, unlike osmium tetroxide, it may be stored for long periods after its container seal has been broken. Like osmium tetroxide, the addition compound of hexamethylene-tetramine and osmium tetroxide is only soluble with difficulty in cold water, but solutions may readily be prepared by first dissolving the compound in the minimum amount of dimethylformamide and then diluting to the desired concentration with distilled water. The complex dissociates and the solution has a vapour pressure of osmium tetroxide similar to aqueous solutions of osmium tetroxide of comparable strength.

We have now found according to the present invention that complexes of osmium tetroxide and certain heterocyclic compounds are useful for the fixing and/or staining of cells in the preparation of specimens for examination by electron microscopy. These complexes are new compounds.

Accordingly, a first aspect of the invention provides complexes of osmium tetroxide and a compound having a heterocyclic ring containing one or two tertiary nitrogen atoms.

Said compound can be an aromatic tertiary amine or a cycloaliphatic tertiary amine. Where it is an aromatic tertiary amine, it can be a heterocyclic compound having only one tertiary nitrogen atom in the heterocyclic ring, for example, isoquinoline, or it can be a heterocyclic compound having two tertiary nitrogen atoms in the heterocyclic ring, for example, pyridazine or phthalazine.

Where said compound is a cycloaliphatic tertiary amine, it can be one having only one tertiary nitrogen atom in the heterocyclic ring, for example, quinuclidine, or it can be a heterocyclic compound having two tertiary nitrogen atoms in the heterocyclic ring, for example, triethylene diamine (i.e. 1,4-diazabicyclo-2,2,2,-octane).

The complexes of the invention are believed to be straight-forward addition complexes and they can be prepared, in general, by adding the heterocyclic compound to an aqueous solution of osmium tetroxide and isolating the product.

Accordingly, in a second aspect, the invention provides a process for the production of osmium tetroxide complex which comprises reacting osmium tetroxide with a compound having a hetrocyclic ring containing one or two tertiary nitrogen atoms, and recovering the resulting product.

The following examples illustrate in detail the preparation of some complexes according to the invention. The amines (heterocyclic compounds) used in these examples are:

| Example | Amine | Structure | Formula |
|---|---|---|---|
| 1 | pyridazine | 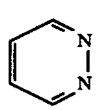 | $C_4H_4N_2$ |
| 2 | phthalazine | 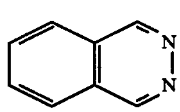 | $C_8H_6N_2$ |
| 3 | isoquinoline | 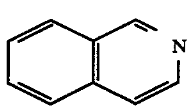 | $C_9H_7N$ |
| 4 | triethylene-diamine |  | $C_6H_{12}N_2$ |
| 5 | quinuclidine |  | $C_7H_{13}N$ |

EXAMPLE 1

Osmium tetroxide (3 g) was dissolved in water (120 ml) at 18°–22° C. Pyridazine (2.2 g) was added dropwise. Yellow crystals were precipitated which were filtered, washed with water and a minimum quantity of ethanol and dried in air. Yield=0.9 (23% of theoretical).

Solubility in dimethylformamide: 420 g. $1^{-1}$.

| Formula of complex: $OsO_4 . C_4H_4N_2$. | | | |
|---|---|---|---|
| Elemental analysis: | C | N | O |
| Calculated | 14.36 | 8.38 | 19.15 |
| Found | 14.30 | 8.40 | 18.62 |

EXAMPLE 2

Osmium tetroxide (5 g) was dissolved in water (200 ml) at 18°–22° C. Phthalazine (2.8 g) was dissolved in water (45 ml) and added to the solution of osmium tetroxide. The resultant yellow crystals were filtered, washed in water and dried in air.

Yield=6.6 g (86% of theoretical)

Solubility in dimethylformamide: 550 g. $1^{-1}$.

| Formula of complex: $OsO_4 . C_8H_6N_2$ | | | |
|---|---|---|---|
| Elemental analysis: | C | N | O |
| Calculated | 25.00 | 7.29 | 16.67 |
| Found | 25.58 | 7.52 | 16.75 |

EXAMPLE 3

Osmium tetroxide (5 g) was dissolved in water (200 ml) at 18°–22° C. and isoquinoline (2.8 g) was added dropwise with stirring over a period of about half an hour. The yellow crystalline product was filtered, washed with water and a minimum volume of ethanol and air dried.

Yield=5.7 g (75% of theoretical).

Solubility in dimethylformamide: 500 g. $1^{-1}$.

| Formula of complex: $OsO_4 . C_9H_7N$ | | | |
|---|---|---|---|
| Elemental analysis: | C | N | O |
| Calculated | 28.18 | 3.65 | 16.70 |
| Found | 28.60 | 3.69 | 16.41 |

EXAMPLE 4

Osmium tetroxide (5 g) was dissolved in water (200 ml) at 18°–22° C. and triethylenediamine (1.1 g) in water (20 ml) was added with stirring over five minutes. The orange-red microcrystalline product was filtered, washed with water and air dried.

Yield = 5.4 g (87% of theoretical).

Solubility in dimethylformamide: 200 g. $1^{-1}$.

| Formula of complex: 2 $OsO_4 \cdot C_6H_{12}N_2$ | | | |
|---|---|---|---|
| Elemental analysis: | C | N | O |
| Calculated | 11.61 | 4.51 | 20.63 |
| Found | 11.63 | 4.52 | 20.32 |

EXAMPLE 5

Osmium tetroxide (5 g) was dissolved in water (200 ml) at 18°–22° C. Quinuclidine hydrochloride (5 g) was dissolved in the minimum quantity of water with sodium hydroxide (1.36 g) present and added to the osmium tetroxide solution with stirring for five minutes. The resultant orange-red crystals were filtered, washed with water and air dried.

Yield = 7.2 g (99% of theoretical).

Solubility in dimethylformamide: 175 g. $1^{-1}$.

| Formula of complex: $OsO_4 \cdot C_7H_{13}N$ | | | |
|---|---|---|---|
| Elemental analysis: | C | N | O |
| Calculated | 23.00 | 3.83 | 17.52 |
| Found | 23.03 | 3.84 | 17.34 |

The infra-red spectra of all the complexes showed characteristic absorptions for osmium-oxygen multiple bonds in the 890–950 $cm^{-1}$ region. All spectra also showed absorptions in the 300–400 $cm^{-1}$ region, probably due to osmium-oxygen bonding.

The complexes according to the invention provide more convenient sources of osmium tetroxide than is afforded by the use of osmium tetroxide itself. The complexes all possess the favourable properties also possessed by the complex formed from osmium tetroxide and hexamethylenetetramine, that is, stability and low vapour pressure of osmium tetroxide at ordinary temperatues.

Complexes of this invention are soluble in dimethyl formamide and can be used, for example, as a solution in that solvent (preferably in a mixture of that solvent with water) in the fixing and/or staining of cells.

In a third aspect, the present invention provides a method of fixing or staining cells in the preparation of specimens for examination by electron microscopy, in which the cells are treated with a complex of this invention.

Solutions of complexes according to the invention may be used in the same way as solutions of osmium tetroxide, that is, they generally provide secondary fixing and staining solutions following a primary fix in glutaraldehyde, for example.

Complexes according to the invention may also be used as replacements for osmium tetroxide in other applications. For example, they may be used to form osmium blacks in electron microscopic cytochemistry. Further, they may be used as replacements for osmium tetroxide in the cis-hydroxylation of olefins. The general procedures for the formation of osmium blacks are described in Data Sheet 180-8/74 by Olysciences Inc., entitled "Osmeth" and the general procedures for the cis-hydroxylation of olefins are described in Organic Chemistry, by I. L. Finar, published by Longmans, Vol 2, 2nd Edition, pages 113, 114, 117.

What we claim is:

1. In a method of fixing or staining cells in the preparation of specimens for examination by electron microscopy, in which the cells are treated with osmium tetroxide, the improvement comprising employing for said osmium tetroxide a complex of osmium tetroxide and a compound having a heterocylic ring containing one or two tertiary nitrogen atoms said compound being selected from the group consisting of pyridazine, phthalazine, isoquinoline, triethylenediamine, and quinuclidine.

2. A method according to claim 1, in which the complex is in solution in aqueous dimethyl formamide.

3. In a method of forming osmium blacks in electron microscopic cytochemistry, which comprises treating cells with osmium tetroxide, the improvement comprising employing for said osmium tetroxide a complex of osmium tetroxide and a compound having a heterocyclic ring containing one or two tertiary nitrogen atoms said compound being selected from the group consisting of pyridazine, phthalazine, isoquinoline, triethylenediamine, and quinuclidine.

* * * * *